(12) United States Patent
Ruetenik (10) Patent No.: US 10,485,215 B2
(45) Date of Patent: Nov. 26, 2019

(54) EQUINE SHOULDER BRACE FOR SLANT LOAD TRAILERS

(71) Applicant: Monty L. Ruetenik, Clear Lake City, TX (US)

(72) Inventor: Monty L. Ruetenik, Clear Lake City, TX (US)

( * ) Notice: Subject to any disclaimer, the term of this patent is extended or adjusted under 35 U.S.C. 154(b) by 284 days.

(21) Appl. No.: 15/411,981

(22) Filed: Jan. 21, 2017

(65) Prior Publication Data

US 2017/0215373 A1 Aug. 3, 2017

Related U.S. Application Data (60) Provisional application No. 62/288,269, filed on Jan. 28, 2016.

(51) Int. Cl.
*A01K 1/06* (2006.01)
*A01K 1/00* (2006.01)

(52) U.S. Cl.
CPC .......... *A01K 1/0613* (2013.01); *A01K 1/0035* (2013.01)

(58) Field of Classification Search
CPC .. A01K 1/0613; A01K 1/0236; A01K 1/0272; B60P 3/04; B61D 3/163
USPC .......... 119/400, 403, 405, 412, 843
See application file for complete search history.

(56) References Cited

U.S. PATENT DOCUMENTS

| 3,197,189 | A | * | 7/1965 | Pemper | B65G 69/001 |
| | | | | | 114/219 |
| 4,470,373 | A | * | 9/1984 | Kesler | A01K 15/02 |
| | | | | | 119/427 |
| 4,548,150 | A | * | 10/1985 | Drewett | E02B 3/26 |
| | | | | | 114/219 |
| 6,895,897 | B1 | * | 5/2005 | Culp | B60P 3/04 |
| | | | | | 119/412 |
| 7,007,632 | B1 | * | 3/2006 | Vrieze | A01K 1/0011 |
| | | | | | 119/14.03 |
| 9,675,043 | B2 | * | 6/2017 | Eriksson | A01K 1/126 |
| 2004/0137210 | A1 | * | 7/2004 | Ochoa | B32B 3/28 |
| | | | | | 428/315.9 |
| 2007/0017457 | A1 | * | 1/2007 | Jackson | A01K 1/0236 |
| | | | | | 119/843 |

FOREIGN PATENT DOCUMENTS

| DE | 2551647 A1 * | 6/1977 | B60P 3/04 |
| FR | 2484959 A3 * | 12/1981 | B60P 3/04 |
| GB | 248903 A * | 3/1926 | B61D 3/163 |

* cited by examiner

*Primary Examiner* — David J Parsley
*Assistant Examiner* — Danielle A Clerkley
(74) *Attorney, Agent, or Firm* — Douglas Baldwin (57) ABSTRACT

Shock-absorbing bumpers that are adapted and configured to be attached to an interior wall of an animal hauling slant load trailer and positioned to contact the shoulder of an equine when the equine is driven forward by a deceleration or braking of the trailer. The bumper(s) are positioned to contact and restrain the equine shoulder allowing it to lean into it, thereby preventing the unnecessary extension of and stress on the animal's right front leg and hoof.

5 Claims, 8 Drawing Sheets

EQUINE SHOULDER BRACE FOR SLANT LOAD TRAILERS

CROSS REFERENCE TO RELATED APPLICATIONS

This application claims benefit of Provisional Patent Application Ser. No. 62/288,269 filed Jan. 28, 2016, the contents and disclosure of which is incorporated herein by reference in its entirety for all purposes.

BACKGROUND

Field of Invention

This invention relates to animal transport trailers and more specifically to equine shoulder braces for equine slant load trailers.

Background

Slant load trailers have become a popular choice of many equine owners in recent years. They have the advantage of not only being able to haul a greater number of horses in a shorter trailer, but they also have seemingly improved the loading procedure because of the slant. These trailers, however, are more suitable for smaller equine than larger ones, and they have contributed to leg injuries. "The original purpose of the slant load trailer was to put more horses into a shorter trailer. Hauling 4, 6, or more horses in a straight load trailer necessitates a very long trailer that many people don't want. The first horses to be hauled in slant loads were quarter horses and polo ponies, smaller horses that could cope with the shorter stall length. A horse that is cramped in a stall is not able to use its head and neck normally to keep its balance in the trailer. If he is hauled in the trailer this way for long periods, he overcompensates and uses improper muscles to cope. A smaller horse in a traditional slant load is able to move around a bit to use his head and neck for balance, and he can also adjust his position somewhat to relieve tired muscles and joints. A horse that fits more tightly doesn't have that option. Why ask a horse to absorb the force of acceleration and deceleration in a trailer in a slanted position where he must use the right foreleg and the left hind leg in an uneven manner? Traveling for long distances in this position can make a horse sore. Sometimes stiffness or soreness that may cause behavioral problems, and outright lameness that is not often attributed to the trailer ride, can be caused by it just the same. Hauling in a straight position, either forward or backwards, helps the horse equally absorb the acceleration and deceleration through the length of the spinal column." Neva Kittrell Scheve: *The Benefits of Slant Load Horse Trailers*. See article at eqispirit.com/index.htm.

The current method of hauling equine in slant load trailers provides a potentially harmful situation for the animal. A shock-absorbing bumper installed on an interior wall and precisely positioned to contact the shoulder of the hauled equine when it is thrown forward upon movement of the vehicle would remedy the issue.

Leg strain can cause serious problems for performance horse that are extensively hauled, for example. Travis Graves, a noted radio team roper, estimates that he hauls horses 70,000 miles each year on the rodeo circuit. Dr. Joe Strickland has reported significant right front leg injuries in slant load trailer hauled horses. "The right front leg in a typical slant load trailer can take a lot of abuse. I see a lot of right front suspensory strains in a conventional slant, and polo wraps supporting those legs make a difference. Soft-Rides help cushion the overall concussion that those legs take." Dr. Joe Stricklin; Spintowinrodeo.com, August 2015.

Others report fatigue and leg injury for slant load hauling. For example: See this comment from "goodhors": "From the farrier angle, husband sees quite a few shipped horses. Often sees the sore horse on right front. This is the leading hoof in all slants we see, hoof horse uses to hold himself in place. Every halt, slow down, turn, puts pressure and weight on that hoof, harder than any of the other hooves. The leg is always in use during slant hauling, gets no rest, does get muscle fatigued. Depending on the commercial hauler or owner's hurry, some horses are dead lame for several days or more after the trip in slant load trailers. Methods of hauling, rest periods, can affect results. This same stiffness/lameness problem is not happening on straight load horses, front or rear facing." Chronicle of the Horse Forum; www-.chronofhorse.com/forum/archive/index.php/t-169995.html. Also further experience with slant load trailer leg injuries: "Why ask a horse to absorb the force of acceleration and deceleration in a trailer in a slanted position where he must use the right foreleg and the left hind leg in an uneven manner? Traveling for long distances in this position can make a horse sore. Sometimes stiffness or soreness that may cause behavioral problems, and outright lameness that is not often attributed to the trailer ride, can be caused by it just the same. Hauling in a straight position, either forward or backwards, helps the horse equally absorb the acceleration and deceleration through the length of the spinal column." Neva Kittrell Scheve; *Debunking Trailer Myths and Half Truths*: Horse and Track Review.com; www.horsetackreview.com/article-display/777.html.

What is needed is a means to reduce the stress on equine legs and muscles and particularly on the right front leg in equines hauled in slant load trailers. The present invention provides shoulder braces or bumpers that are easily installed in slant load equine trailers and are effective in reducing leg injuries while transporting horses.

DETAILED DESCRIPTION

In broad scope, the invention is a shock-absorbing bumper adapted and configured to be attached to an interior side wall of a slant load trailer and positioned to contact the shoulder of equine when it is driven forward by a deceleration or braking of the trailer. The bumper is positioned to contact and restrain the equine shoulder allowing it to lean into the bumper, thereby preventing unnecessary extension of and stress on the animal's right front leg and hoof. The invention is also a method of reducing equine leg stress during slant load trailer hauling.

Figure 1:
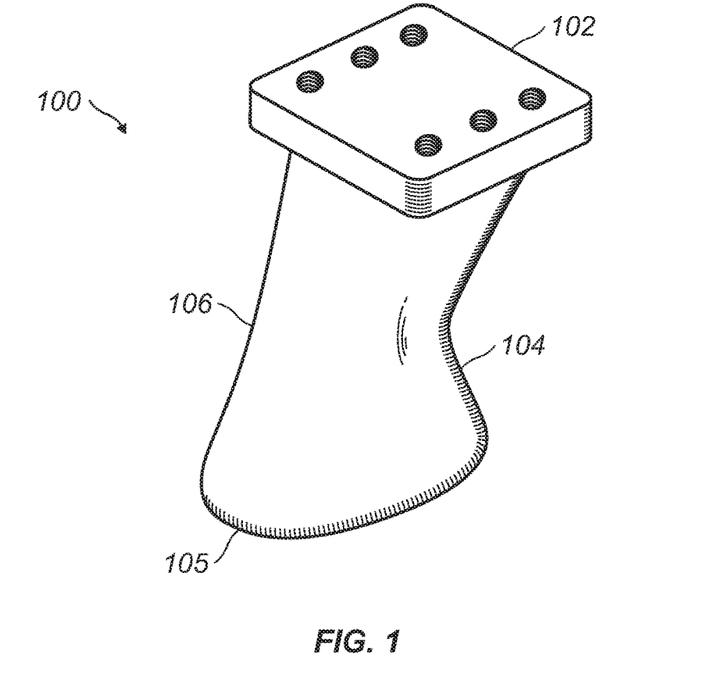
FIG. 1 is a perspective view of an embodiment of the invention.
Figure 2:
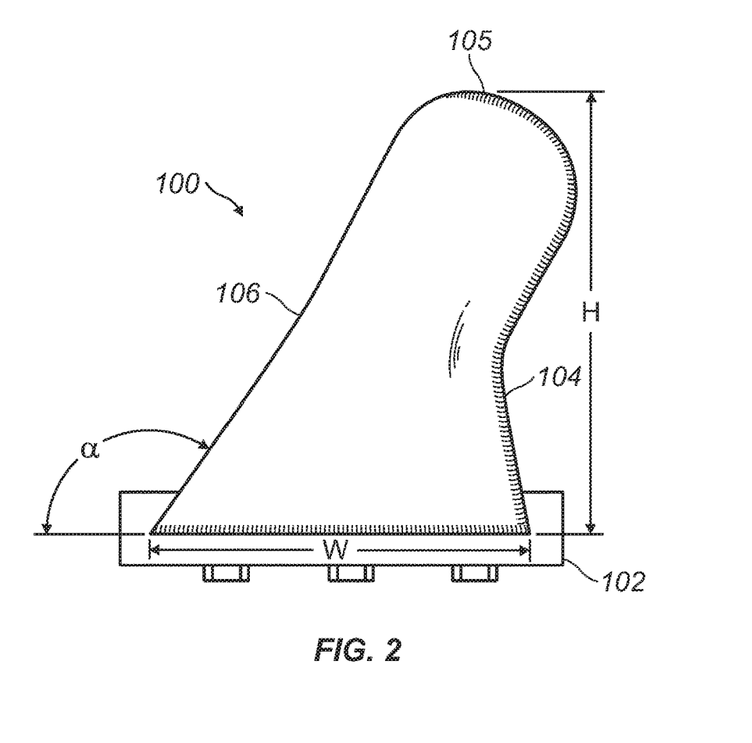
FIG. 2 side view of an embodiment of the invention.

Referring to the Figures, FIG. 1 illustrates a first set of embodiments of the equine slant load trailer bumper of the invention. The bumper, 100, is an elongated structure having a substantially straight rear side, 106, and an opposite side (front) with a centered concave slope, 104. The concave side is designed to approximate the slope of an equine shoulder. The bumper has a rounded distal end, 105, and an attachment plate 102 on the proximal end. FIG. 2 shows some dimensions of an embodiment. In a prototype, the length H is 7.5 inches and the width W is 7.5 inches. In general width W can be from about 10 to about 28 inches with 10 to 18 inches being optimal. It is preferred that the sides of the bumper be sloped as illustrated but the may be straight. FIG. 2 illustrates slope angles where the angle of slope from the plane of the base or attachment plate of the structure. The angle a will be from about 90° to 130° (0 to 40° from vertical).

The bumper may suitable be made of molded elastomeric polymer. It needs to be relatively hard and rigid, but not completely so. Molded polyurethane is very suitable and convenient to work with. It is preferred that thermoplastic polyurethane of about 45 to 75 Shore A hardness be used, with Shore A hardness of about 65 being especially suitable. Polyurethanes are particularly suitable material for the bumper as they are easily moldable in open molds or by injection molding. Other polymer materials with similar characteristics as polyurethane, such as polyvinyl chlorides, styrene butadiene styrene polymer, epoxies and the like, are also usable. Choice of these will be well within the ability of those skilled in the polymer art to select.

The attachment plate, 102, may be constructed of wood such as plywood, particle board, fiber board, MDF, hard polymer, metal, and the like. The general requirement for the attachment material is that the plate be sufficiently strong to be securely attached to a trailer wall and to the body of the bumper. The attachment will be securely attached to the body of the bumper, as by bolts and nuts (See FIG. 4), adhesive, or molded together with the body of the bumper. The bumper may also be strengthened by a more rigid and stronger plate or sheet and positioned on the back (away from the equine) of the bumper.

The bumper, if made of polymer, may be reduced in weight by adding low density small particles into the polymer such by the technique described in U.S. Pat. No. 8,656,691, U.S. patent Application 2014/0033661 and U.S. patent Application 2015/0088042, the disclosures of which are incorporated n herein by reference. The particles may be any material with sufficient flexibility and durability for incorporation into a bumper structure. In a preferred embodiment wherein the polymer of the solid member is polyurethane, the particles materials are of lower density than elastomeric polyurethane, capable of being adhered to by elastomeric polymer materials (preferably polyurethane), and generally spherical or elliptical in shape. Suitable materials may include, but are not limited to, polymers and elastomers, and preferably expanded foam or cellular formulation of these polymers. Specific examples include polypropylene and expanded polypropylene (PP), polyethylene and expanded polyethylene (PE), high density polyethylene (HDPE), ethylene propylene diene monomer (EPDM), polystyrene (PS), polyurethane and polyurethane foams, polystyrene, polybutadiene, styrene-butadiene rubber (SBR), and polyvinyl chloride. In one embodiment, polypropylene and polyethylene are preferred, with closed-cell expanded polypropylene being particularly preferred for its low density, high durability, flexibility, resilience, and thermal insulation. Expanded polyurethanes are also very suitable. The characteristics of these mixed polymer materials and methods of molding are fully described in U.S. Pat. No. 8,656,691, U.S. patent Application 2014/0033661 and U.S. application 2015/0088042 and are equally applicable for the bumpers of this invention. The disclosure of the patent and applications are incorporated herein by reference.

Figure 3:
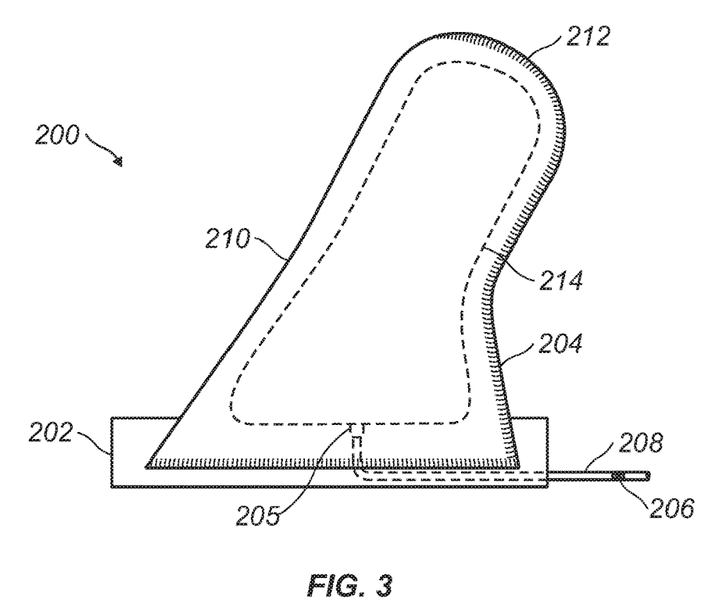
FIG. 3 is side view of another embodiment of the invention.

FIG. 3 illustrates an inflatable bumper 200. This embodiment has an inflatable bladder 214 disposed in an outer casing that has a rear side 210, a concave front side 204, an attachment plate 202 and a rounded distal end 212. The inflatable bladder has an inflation conduit 208 connected to the bladder by connection 205 and a valve 206.

The bladder will have at least one inlet port, 205/206. When air or other gas is the pressurizing fluid used, the bladder can be both pressurized and depressurized through a single, two-way valve. The preferred valve type for the bladder inflation is those valves used in tires—Schrader or American valves or Presta valves. Presta valves are suitable and preferred for higher pressures and when the bladder is to remain inflated for longer periods of time. Both these valve types allow the bladder to be easily inflated with air (as from an air pump such as a customary tire pump) and as easily deflated. They also aid in making the assembly lightweight and portable without the need for external power sources. The bumpers may also be adapted from boat fender units such as Taylor or Shoreline vinyl inflatable boat fenders as explained below in a second set of embodiments. These would not be angled as described above and would need to be fitted with an attachment plate but could otherwise be suitable.

Figure 4:
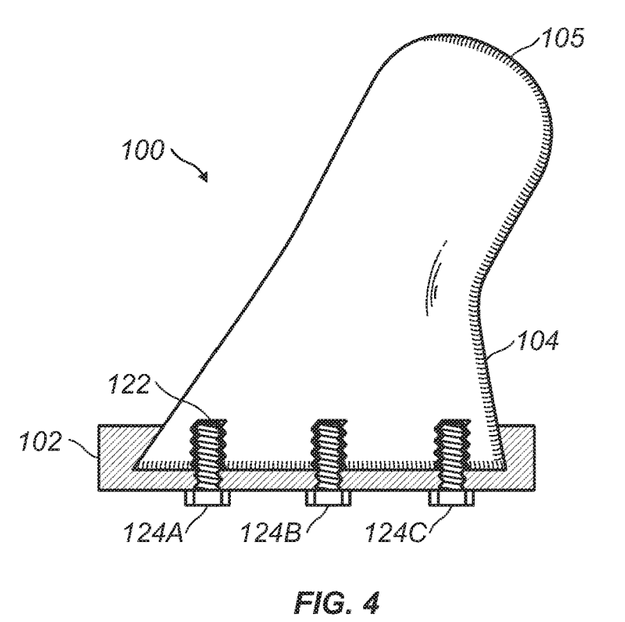
FIG. 4 is a side view of another embodiment of the invention.

FIG. 4 illustrates an embodiment of an attachment means for the bumper to the attachment plate 102. Nuts 122 are embedded in the bumper and the plate attached by bolts 124A, 124B and 1245C. The bolts may be passed through the walls of trailer stall (304 in FIG. 5) to secure the bumper to the trailer inter wall. The plate may have, alternatively, straps or sheet of hook and loop material, one side attached to the attachment plate and the other to the wall inside wall of a slant load trailer. Rails on which tracks can slide may also be used to provide a vertically adjustable attachment.

Figure 5:
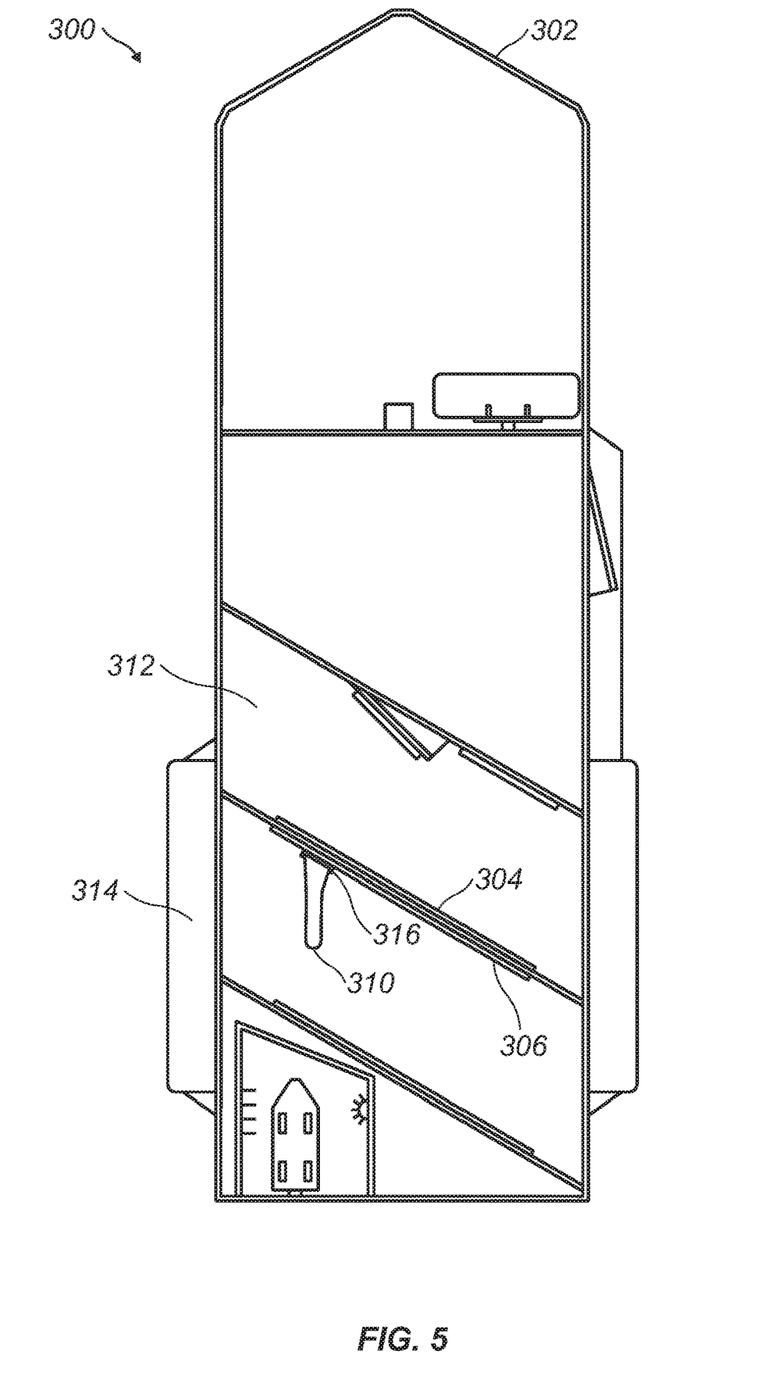
FIG. 5 is a top view of a slant load trailer showing placement of an embodiment of the invention.

FIG. 5 illustrates placement of the bumper, 310, in a slant load trailer 300. The bumper 310 is attached to a trailer side wall 304 through plate 316 in slant stall 314. 312 is a second stall that is typical of such trailers. The bumper will be place at a height to approximate the shoulder height of the equine being hauled. As described above, the plate 316 may be attached to the wall 304 by bolts through holes drilled in the wall. The plate may also be attached by straps or a sheet of hook and loop attachment material or on an interconnecting rail system so as to be adjustable for height.

A second set of embodiments are illustrated in FIGS. 6-12.

As shown in FIGS. 9A, 9B, 10A, 10B and 10, 11A and 11B the assembly comprises a bumper, 500, fitted into holder structure 400.

As illustrated in the Figures, suitable bumpers are basically cylinders with a straight section of about 18-32 inch length ending with a bent (or knee) section, 502, at the proximal end that is tapered, 508, to form a small cross section rectangle. The preferred bumper shape is square with rounded corners, but round or oval shaped structures are also acceptable. It is preferred that the bumper be inflatable to allow variation in the "softness" of the bumper. The rounded proximal end (502) will contact the equine's (700 in FIG. 12) right shoulder when the assembly is in use as illustrated in FIG. 12 (702 is the equine shoulder).

The end of the small-diameter, rectangular bumper end will preferable be relatively solid and have a center hole for attachment to the receptacle (such as the hole for attachment by rope to a dock in the commercial boat version). The bent or knee section, 502, will be bent about 30 to 100° from the plane of the straight section with about 90° being preferred. The bumpers are made of any suitable elastomeric material such as polyvinyl chloride (vinyl), polyethylene, EPDM, silicone and the like. The commercially available bumpers are made of high strength marine vinyl (polyvinyl chloride). It is preferred that they be inflatable as are commercial boat bumpers from Taylor Made Products. The commercial boat bumpers specify a pressure of about 2-2.5 psi pressure for the vinyl bumpers. Very suitable commercially available boat bumpers are available from Taylor Made Products as Low Preboard Benders (http://www.taylormadeproducts.com/cgi-bin/catalog.pl?item_id=9). These boat bumpers are available in various colors and in two sizes (5 inch diameter by 14 inch length and 7 inch diameter by 23 inch length). The 5 inch diameter, 14 inch length bumper is generally preferred.

Figure 6A:
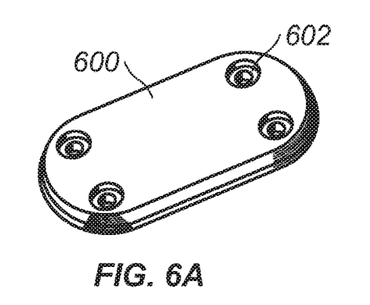
FIG. 6A is a perspective view of an embodiment of a backing plate for use on the opposite wall of a trailer to attach the bumper holder showing the two layers and bolt holes with recesses.
Figure 6B:
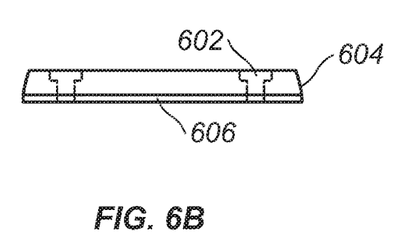
FIG. 6B is a side view of an embodiment a backing plate for use on the opposite wall of a trailer to attach the bumper holder of showing the two layers and bolt holes with recesses
Figure 7:
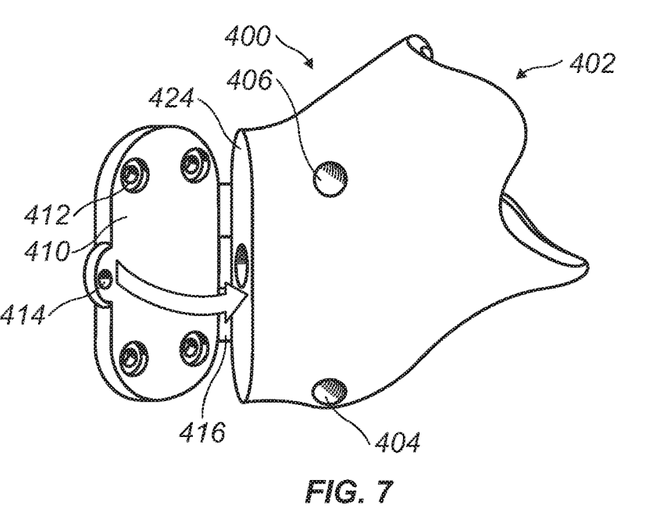
FIG. 7 is a perspective view of a bumper holder of an embodiment of the invention.
Figure 8:
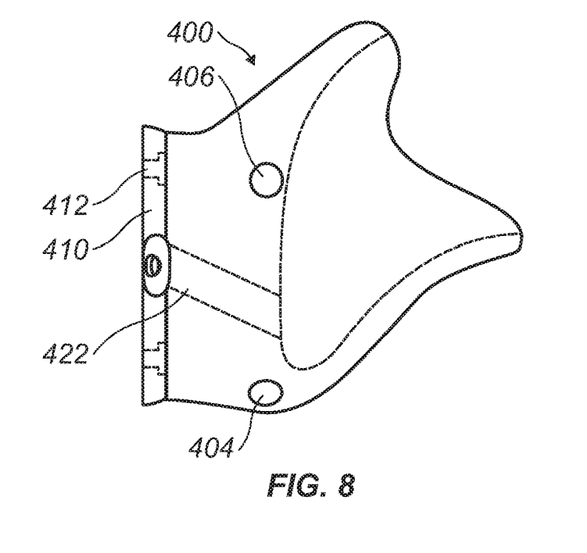
FIG. 8 is a side view of a bumper holder of an embodiment of the invention.

As shown in FIGS. 10A, 10B, 11A, 11B and 12) the assembly comprises a bumper as described above and a bumper holder, 400, an optional hinged plate, 410, and optionally a backing plate, 600, for use on the opposite side of a trailer wall to which the assembly is attached. A backing plate is shown in FIGS. 6A and 6B. It has countersunk holes, 602, for bolts used to attach through the trailer wall to the bumper holder hinged plate 410. It is also preferably a dual layer construction with a hard layer (Shore A of about 95) on top, 604, and softer layer (Shore A of about 65).

Figure 10A:
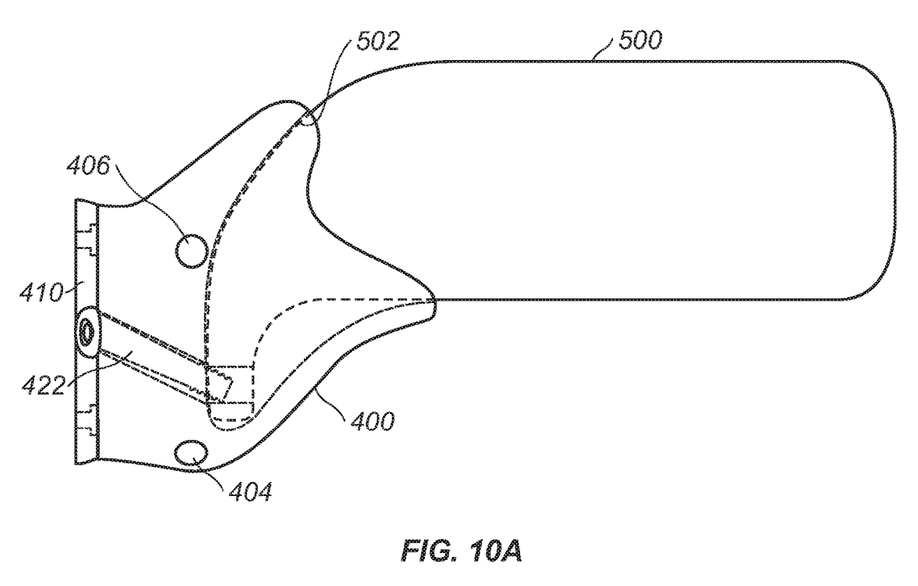
FIG. 10A is a side view of the bumper assembly of an embodiment of the invention.
Figure 10B:
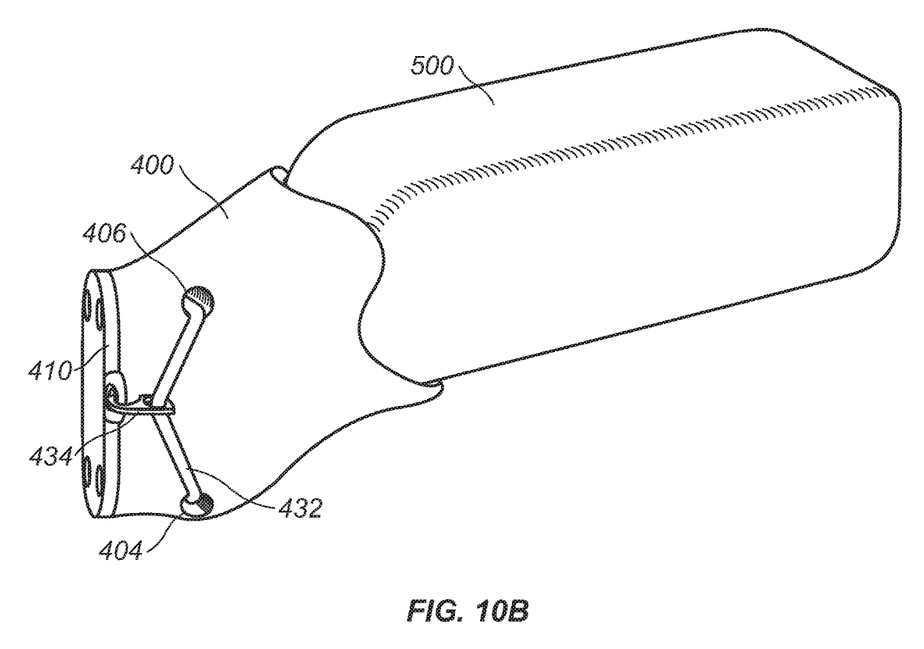
FIG. 10B is a perspective view of the bumper assembly of an embodiment of the invention.
Figure 12:
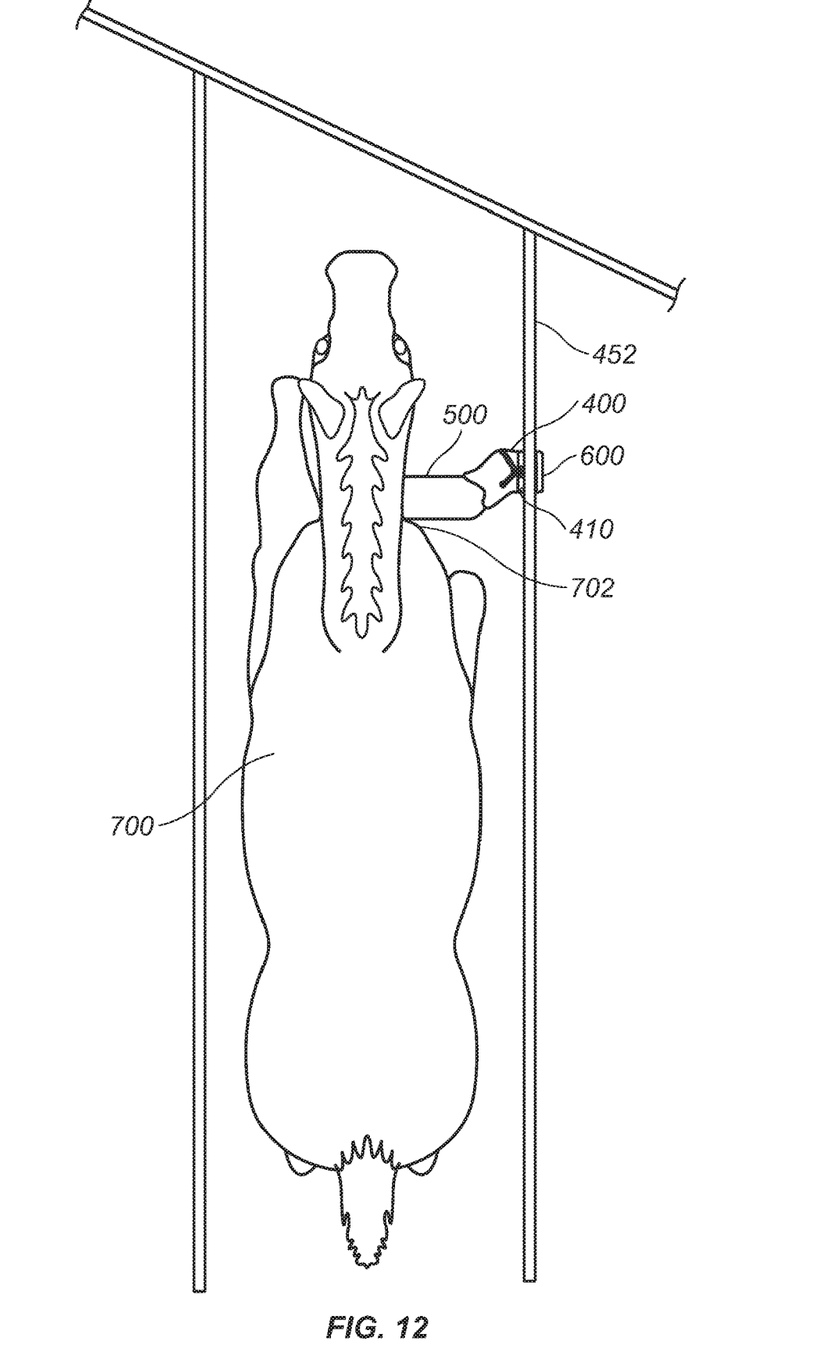
FIG. 12 is a top view of the bumper assembly of an embodiment of the invention disposed in a slant load trailer with an equine in position.

The bumper holder structure 400 has a hollow section, 402, shaped to accept the proximal tapered end of the bumper used in the assembly as shown clearly in FIGS. 10A, 10B and 12. It is structured and shaped to allow the straight side of the bumper to extend beyond the holder structure as shown in FIGS. 10A and 10B. This prevents the equine shoulder from direct contact with the odd shaped and hard bumper holder structure and allows contact only with the bumper proper. It is expected that the equine shoulder will be forced against the bumper when the trailer pull is braked but also it is likely that an equine will lean against the bumper even when the trailer is a rest or moving smoothly (see FIG. 12).

Figure 9A:
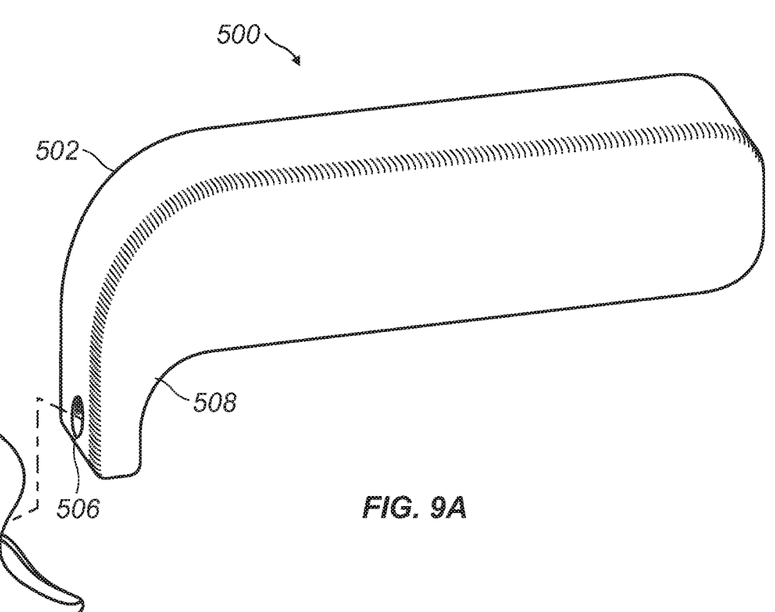
FIG. 9A is a perspective view of a bumper of an embodiment of the invention.
Figure 9B:
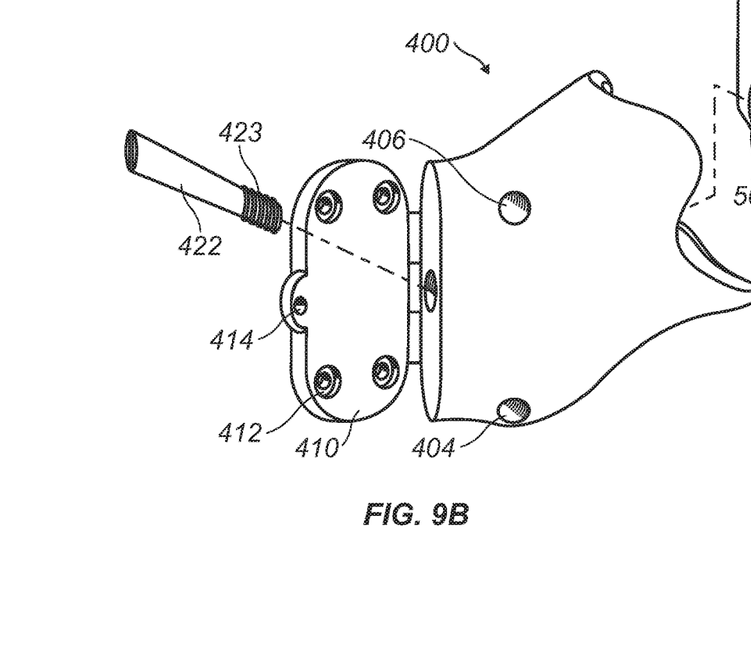
FIG. 9B is a perspective view of a bumper holder of an embodiment of the invention.

In one embodiment the bumper, 500, is held into place in the bumper holder, 400, by inserting a pin, 422, through an opening in the holder structure through the hole, 506, in the bumper as illustrated in FIGS. 9B and 10A. Generally the pin will be sized to be completely covered by the opening in the bumper holder when it is in place. The pin may be threaded, 423, to mate with female threads in the recess of the bumper holder as shown in FIG. 10A. A threaded pin will optionally have a slot in the end opposite the threaded end to allow it to be turned with a screw driver blade. The bumper holder, 400, may optionally have holes 404 and 406 to accommodate an elastic cord for a hinged embodiment detailed below.

Figure 11A:
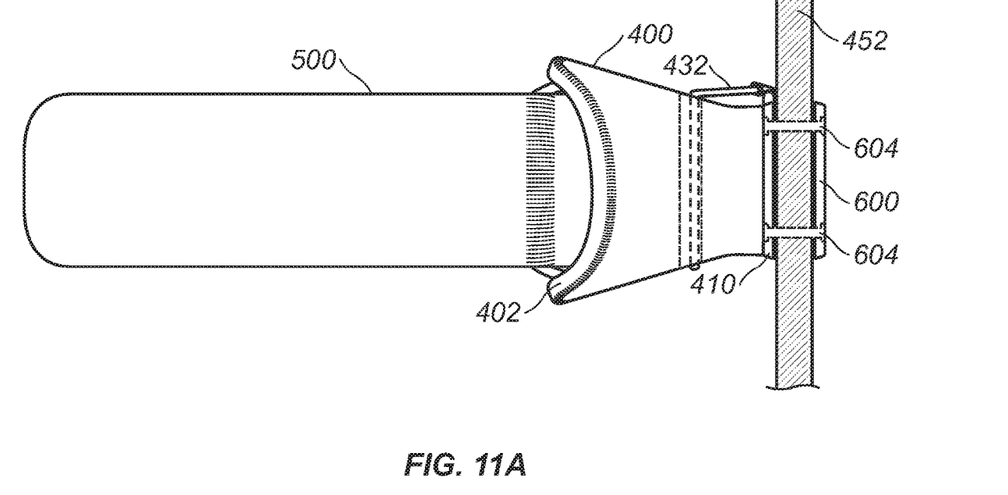
FIG. 11A is a top view of the bumper assembly of an embodiment of the invention.
Figure 11B:
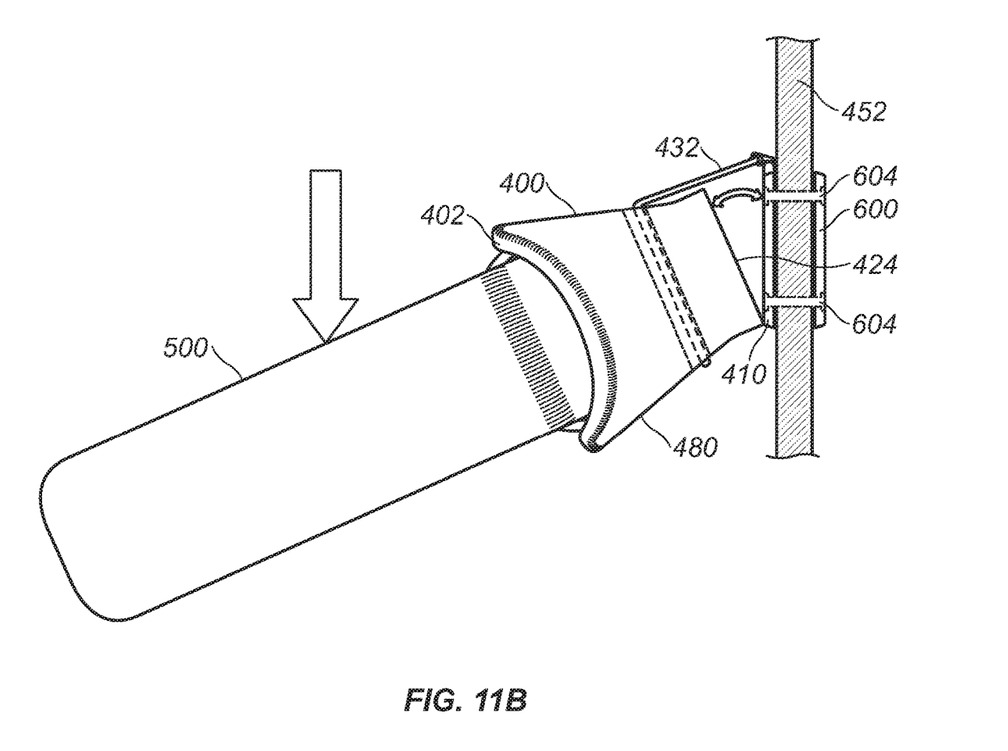
FIG. 11B is another top view of the bumper assembly of an embodiment of the invention.

The bumper holder, 400, embodiment illustrated in the FIGS. 7, 8, 10A, 10 B 11A, 11B, has a flat proximal face 424 (FIG. 11B) and structured distal edges, 402, shaped to provide space for and curvature around an inserted bumper and around an air injection valve inserted in the bumper—see FIGS. 10B, 11A and 11B. The bumper holder structure face, 424, may be permanently attached directly to a trailer wall or attached to a bumper support (410) that is adapted to be attached to a trailer wall. The bumper holder may also be removable It is preferred that the bumper holder face, 424, and support, 410, be hinged to allow the bumper assembly to be folded out of the center of the trailer space. For the hinged embodiment there is molded (or otherwise attached) into proximal holder face, 424, a flexible hinge, 416 (FIG. 7) that has the opposite side molded (or otherwise attached) to the holder support 410. This allows the holder support 410 to be attached to the wall of a trailer with the bumper support attached but hinged to allow it to be folded out of the center of the trailer space. This is desirable since the internal trailer walls are removable. The hinge, 416, is preferably configured to allow the bumper holder structure (and bumper) to be folded down against the trailer wall as is illustrated in FIGS. 11 A and 11B (the wall 452 is shown in vertical orientation). The hinge may be any suitable construction such as commercial metal hinges, but it is preferred that the hinge be fabric and especially preferred that it be fabric and constructed of Nylon ballistics cloth or Dyneema™. Nylon ballistic cloth is generally very tough and durable fabric made with a "ballistic weave", typically a 2×2 or 2×3 basket weave. It can be woven from nylon yarns of various denier such as 840 denier and 1680 denier. Dyneema and Spectra™ are Ultra-high-molecular-weight polyethylene fabrics that are gel spun through a spinneret to form oriented-strand synthetic fibers with yield strengths as high as 2.4 GPa (350,000 psi) and specific gravity as low as 0.97 (for Dyneema SK75).

As shown in FIGS. 9B and 10B the bumper holder support, 410, has a projection in the side opposite the hinge with a hole, 414. This is to accommodate the flexible latching mechanism that, in one embodiment, holds the bumper assembly in place when in use. The support also has holes 412 with countersunk opening so that bolt heads or nuts used to secure it into place will be beneath the surface of the support. It is an important feature of the entire construction of the bumper assembly that all sharp or rough projections be covered to protect an equine from injury.

The hinged bumper holder embodiment assembly requires means to hold the bumper holder and holder support together when in use. This may be accomplished by any number of ways, including hook and loop straps, latches, pins and a bolt and nut arrangement. One such preferred means is illustrated in FIGS. 10B, 11A and 11B and 12. Referring to FIG. 10B the bumper holder structure, 400, has holes 404, and 406 through which can be inserted an elastic cord 432, which is threaded through an opening in latch (clip) 434. On the opposite side of the structure the elastic cord is joined together by clips or other suitable means to hold the cord tightly against the structure. The clip 434 is hooked into the opening 414 to hold the assembly into proper alignment against the trailer wall (See FIG. 9B). Suitable elastic cords are fabric covered elastic material such "shock cord" as used in bungie cords and in marine use. Generally ¼ to ¾ inch diameter nylon or polyester covered cords are suitable. A ⅜ inch diameter marine "shock cord" was successfully used in a prototype. These cords are readily available form marine suppliers such as West Marine (www.westmarine.com/shock-cord). The latch (clip) as shown in FIG. 10B is a modified "shock cord" clip, but may be any suitable configuration to connect the cord to the bumper holder support. It may, for example be hook and loops straps, S hooks, various latches and the like. The use of this elastic cord embodiment provides connection means for the assembly that is sufficiently flexible in the event an equine rears onto or otherwise gets atop the structure it will bend downward so as to not entangle or injure the equine. As with other features this is important to ensure that the assembly does not injure the equine user.

The bumper holder, 400, may be made of molded elastomeric polymer. It needs to be relatively hard and rigid, but not completely so. Molded polyurethane is very satisfactory and convenient to work with. It is preferred that thermoplastic polyurethane of about 45 to 75 Shore A hardness be used, with Shore A hardness of about 65 being especially suitable. Polyurethanes are particularly useful materials for the bumper as they are easily elastic, moldable in open molds or by injection molding. Other polymer materials with similar characteristics as polyurethane, such as polyvinyl chlorides, styrene butadiene styrene polymer, epoxies and the like, are also usable. Choice of these will be well within the ability of those skilled in the polymer art to select.

As in the bumpers of the first set of embodiments the bumper holder, 400, if made of polymer, may be reduced in weight by adding low density small particles into the polymer such by the technique described in U.S. Pat. No. 8,656,691 and US patent Application 2014/0033661 the disclosures of which are incorporated herein by reference. The particles may be any material with sufficient flexibility and durability for incorporation into a bumper structure. In a preferred embodiment wherein the polymer of the solid member is polyurethane, the particles materials are of lower density than elastomeric polyurethane, capable of being adhered to by elastomeric polymer materials (preferably polyurethane), and generally spherical or elliptical in shape. Suitable materials may include, but are not limited to, polymers and elastomers, and preferably expanded foam or cellular formulation of these polymers. A volumetric concentration of particles in the polymer will be in the range of ten to forty-five (10-45) percent, with a preferred range of about twenty to forty (20-40) percent, and a more preferred range of about thirty to forty (30-40) percent. Specific examples of suitable particles include polypropylene and expanded polypropylene (PP), polyethylene and expanded polyethylene (PE), high density polyethylene (HDPE), ethylene propylene diene monomer (EPDM), polystyrene (PS), polyurethane and polyurethane foams, polystyrene, polybutadiene, styrene-butadiene rubber (SBR), and polyvinyl chloride. In one embodiment, polypropylene and polyethylene are preferred, with closed-cell expanded polypropylene being particularly preferred for its low density, high durability, flexibility, resilience, and thermal insulation. Expanded polyurethanes are also very suitable. The characteristics of these mixed polymer materials and methods of molding are fully described in U.S. Pat. No. 8,656,691, US application 2015/0033661 and are equally applicable for the bumper holder structures of this invention. The disclosure of this patent and applications are incorporated herein by reference.

The current method of hauling equine in slant load trailers provides a potentially harmful situation for the animal. A shock-absorbing bumper installed on an interior wall and precisely positioned to contact the shoulder of the hauled equine when it is thrown forward upon deceleration or other movement of the vehicle will remedy the issue. Bumpers useful for this service are constructed as describe above. In use the bumper will be attached to the interior wall of a trailer and folded down to prevent interference will loading an equine. When the equine is in place the bumper will he lifted into position and latched into place.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded as illustrative rather than a restrictive. Therefore, the scope of the invention should be limited only by the appended claims.

The invention claimed is:

1. An equine shoulder bumper assembly comprising;
   a. a bumper comprising a cylinder with a straight section ending with a tapered end section, the tapered end section being disposed at an angle to the centerline of the straight section at the proximal end and forms a small cross section rectangle shape;
   b. a bumper holder structure having a hollow section shaped to accept the tapered end section of the bumper and structured and shaped to allow the straight section of the bumper to extend beyond the holder structure and having a flat face opposite the hollow section; and
   c. a bumper holder mounting plate attachable to the flat face of the bumper holder structure and that is adapted to be attached to a vertical wall of a slant load trailer, and wherein the holder mounting plate is attached by hinge to the flat face of the bumper holder structure.

2. The equine shoulder bumper assembly of claim 1 wherein the hinge is constructed from fabric selected from Nylon ballistics cloth, Dyneema™ and Spectra™.

3. The equine shoulder bumper assembly of claim 1 wherein the bumper holder mounting plate attachable to the flat face of the bumper holder structure is attached to a vertical wall of a slant load trailer.

4. The equine shoulder bumper assembly of claim 1 wherein the bumper is an inflatable slanted boat dock bumper that is fully enclosed and hollow and that has a valve for inflating.

5. An equine shoulder bumper assembly comprising:
   a. a bumper comprising a cylinder with a straight section ending with a tapered end section, the tapered end section being disposed at an angle to the centerline of the straight section at the proximal end and forms a small cross section rectangle shape;
   b. a bumper holder structure having a hollow section shaped to accept the tapered end section of the bumper and structured and shaped to allow the straight section of the bumper to extend beyond the holder structure and having a flat face opposite the hollow section; and
   c. a bumper holder mounting plate attachable to the flat face of the bumper holder structure and that is adapted to be attached to a vertical wall of a slant load trailer, and wherein the flat face of the bumper holder structure is removably secured to the bumper holder mounting plate by elastic cords and latch that engages an opening in the side of the bumper holder mounting plate.

* * * * *